United States Patent [19]

Holtkamp

[11] Patent Number: Plant 5,617

[45] Date of Patent: Dec. 31, 1985

[54] AFRICAN VIOLET PLANT NAMED NEW MEXICO

[75] Inventor: Reinhold Holtkamp, Isselburg, Fed. Rep. of Germany

[73] Assignee: Gessellschaftsvertrag uber die Ergindergemeinschaft "Optimara", Rees Haffen, Fed. Rep. of Germany

[21] Appl. No.: 477,690

[22] Filed: Mar. 22, 1983

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

An African violet plant named New Mexico having vigorous growth and upright flower stems, lilac colored, frilled and undulated flowers with a dark lilac margin and center; 7–10 large flowers per stem, and long lasting, non-dropping habit.

1 Drawing Figure

The present invention comprises a new and distinct cultivar of African violet plant, botanically known as *Saintpaulia ionantha*, and hereinafter referred to by the cultivar name New Mexico.

The new cultivar was referred to during the breeding and selection process by the designation d 113/1, and is a product of a planned breeding program.

The new cultivar was originated from a cross made in a controlled breeding program in Isselburg, West Germany. The female, or seed parent was a cultivar designated B 229/6 pink. The male, or pollen parent was a cultivar designated A 56 M blue.

The new cultivar New Mexico was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

New Mexico has not been observed under all possible environmental conditions. The phenotype may vary significantly with variations in environment such as temperature, light intensity and day length. The following observations, measurements and values describe the new cultivar as grown in Isselburg, West Germany, under greenhouse conditions which close approximate those generally used in commercial practice.

The following traits have been repeatedly observed and are determined to be basic characteristics of New Mexico, which in combination distinguish this African violet as a new and distinct cultivar:

(1) Upright flower stems.

(2) Lilac colored, frilled undulated flowers with dark lilac margin.

(3) Dark lilac center mainly on upper two small petals.

(4) Vigorous growth habit.

(5) Large flowers, 7–10 per stem.

(6) Long lasting, non-dropping flowers.

The accompanying photographic drawing shows a typical specimen plant of the new cultivar. The colors appearing in the photograph are as true as possible with color illustrations of this type.

In the following description, color references are made to The Horticultural Colour Chart (H.C.C.) issued by Wilson Colour Ltd., except where general colors of ordinary significance are referred to. Color values were taken under natural light conditions approximately mid-day in Nashville, Tenn.

Botanical classification: *Saintpaulia ionantha*, Ramat. cv. NEW MEXICO

Parentage:

*Male parent.*—A 56 M blue.

*Female parent.*—B 229/6 pink.

Propagation: The new cultivar holds its distinguishing characteristics through successive propagations by leaf cuttings and by division of shoots.

Plant: From 6 cm. to 10 cm. tall when grown in pots, and approximately 25 cm. in diameter when fully grown.

*Leaves.*—General form: Broadly ovate.

*Diameter.*—50–60 mm.

*Texture.*—Soft.

*Aspect.*—Slightly hairy; shiny.

*Veins.*—Pronounced.

*Color (upperside).*—Ivy green 001060/3.

*Color (underside).*—Greenish-purple.

*Petiole.*—Purplish green.

Flowers:

*Bud.*—Bell shape, 7–10 in number.

*Sepals.*—5 in number. Color: Brownish green. Aspect: Flat, funnel shape. Peduncle: Short, strong, hairy, purplish green.

*Individual flowers.*—Size: 35–45 mm. Color: Upperside: Violet 36/2. Underside: Heliotrope 636/2. Borne: Upright on short pedicel. Shape: Violet shaped, undulated and frilled. Corolla: Compact flower bouquet, 6–9 flowers. Flowering time: 8–10 weeks after potting.

Reproductive organs:

*Anthers.*—2 compound of 4 cells.

*Styles.*—Violet in color; base light green and hairy.

*Pollen color.*—Dresden yellow 64.

Roots: White when young and active; brownish when older.

Disease resistance: Good as known to date.

General observations: Eight (8) weeks after potting New Mexico is well developed and compact, with strong upright flower stems which carry 7–10 buds and few open flowers. Two weeks later the flower head is fully open. The dark margin around the flower and the dark center are unique.

I claim:

1. An African violet plant named New Mexico, as described and illustrated, and particularly characterized by its vigorous growth habit and upright flower stems, lilac colored, frilled and undulated flowers with dark lilac margin and 7–10 large flowers per stem, and by its long lasting, non-dropping habit.

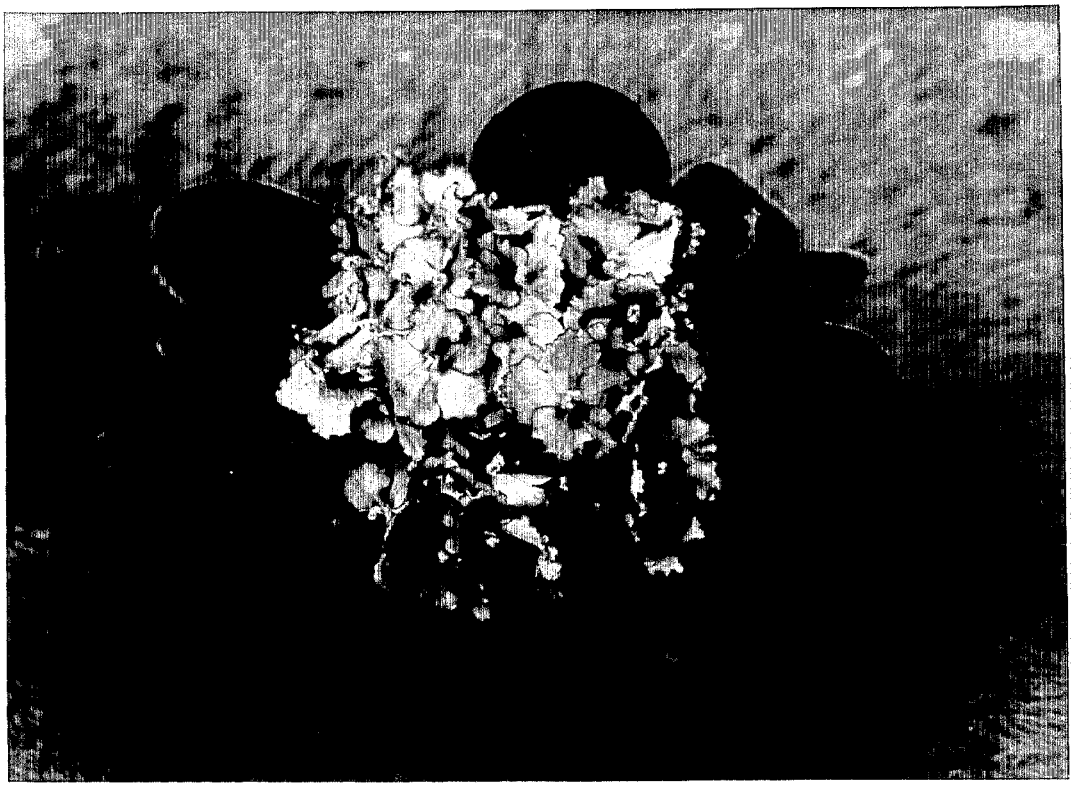

* * * * *